United States Patent [19]

Müller

[11] Patent Number: 5,106,757
[45] Date of Patent: Apr. 21, 1992

[54] PROCESS FOR THE VISUALIZATION OF SUBSTANCE STAINS ON LAYER CHROMATOGRAMS

[75] Inventor: Walter Müller, Neuwied, Fed. Rep. of Germany

[73] Assignee: LTS Lohmann Therapie-Systeme GmbH & Co. KG, Neuwied, Fed. Rep. of Germany

[21] Appl. No.: 725,371

[22] Filed: Jun. 27, 1991

Related U.S. Application Data

[63] Continuation of Ser. No. 479,305, Feb. 13, 1990, abandoned.

[30] Foreign Application Priority Data

Feb. 25, 1989 [DE] Fed. Rep. of Germany ....... 3905954

[51] Int. Cl.$^5$ ............................................. G01N 30/94
[52] U.S. Cl. ..................................... 436/162; 422/57; 422/70; 436/170; 73/61.1 C; 210/658
[58] Field of Search ................. 422/70, 55-57; 73/61.1 C; 436/162, 169, 170; 210/658

[56] References Cited

U.S. PATENT DOCUMENTS

| | | | |
|---|---|---|---|
| 3,630,957 | 12/1971 | Rey et al. | 252/408 |
| 3,975,162 | 8/1976 | Renn | 23/253 TP |
| 4,861,711 | 8/1989 | Friesen et al. | 436/7 |
| 4,861,712 | 8/1989 | Bartl et al. | 435/13 |

Primary Examiner—Robert J. Hill, Jr.
Assistant Examiner—David Redding
Attorney, Agent, or Firm—Sprung Horn Kramer & Woods

[57] ABSTRACT

The present invention relates to a process for the visualization of substance stains on dry layer chromatograms without further addition of a mobile phase, which device has foil of at least one layer and comprises one or more reagents for the visualization of substance stains.

9 Claims, 1 Drawing Sheet

PROCESS FOR THE VISUALIZATION OF SUBSTANCE STAINS ON LAYER CHROMATOGRAMS

This application is a continuation of application Ser. No. 479,305, filed Feb. 13, 1990 now abandoned.

DESCRIPTION

The present invention relates to a device and to a process for the visualization of substance stains on layer chromatograms.

Layer chromatography is a common method for the analytical and preparative separation of complex substance mixtures. In the sense of the present invention layer chromatography means all chromatographic methods in which the stationary phase exhibits a substantially two-dimensional geometry. The layer chromatography is a physico-chemical separation process in which a separation layer (stationary phase), which mainly consists of fine-grain material, is located on an areal carrier. This carrier usually is a glass plate, or a foil consisting of aluminium or polyamide.

The mixture to be separated is applied in dissolved condition in the form of spots or bands on one end of the plate, the so-called starting side, and the plate is usually then placed with the starting side in a special tight-fitting chamber containing a suitable solvent (mobile phase). Due to capillary forces this solvent spreads, starting from the starting side, in the direction of the other side of the plate. In this connection, the substance components applied are taken along for a distance which is characteristic of each substance under the individual conditions. The lower the affinity of the substance for the stationary phase, the longer the distance covered on the plate, which the substance is taken along by the mobile phase. Subsequent to this so-called process of development, the plate is dried, and the stains of the individual substance components are marked. This can be made easily, if the components exhibit a self-colour. Since this case is very rare, it must be ensured by special methods that the substance stains are converted into a somehow dyed or fluorescent form, or that they contrast in another form with the rest of the surface of the stationary phase.

A common method is to add a so-called fluorescence indicator to the stationary phase. The fluorescence is made visible by UV-radiation of a suitable wave-length. If the substance is able to quench this fluorescence, the substance stains are visible as dark areas on a light background.

Since however, by far not all substances are able to quench the fluorescence of the indicator, the conversion of the substance stains into dyed or fluorescent compounds plays at least the same important role. After development has taken place, the chromatography plate is sprayed with the reagent or dipped into a solution of the reagent.

Above all, the spraying method is difficult, since it must frequently be worked with toxic or caustic substances, and contamination of the operator or the laboratory equipment, respectively, cannot completely be prevented. A further disadvantage is that it is only hardly possible to spray the whole plate evenly with the reagent, and thus the quantitative assessment of the chromatograms is impaired. The method of dipping bears the disadvantage that relatively large amounts of reagent solution are necessary, and there is the danger that the solution becomes poor of reagent after repeated use.

It is accordingly the object of the present invention to provide a possibility to visualize substance stains on developed chromatography plates; the invention does not exhibit the disadvantages of the methods described hereinbefore, i.e., can do without spraying toxic or caustic substances; comparatively low amounts of reagent are needed, and nevertheless it makes possible to bring into even contact the whole surface of the stationary phase with the reagent.

Surprisingly, this object is achieved by a foil having at least one layer, which foil exhibits at least one layer comprising one or more reagents for the visualization substance stains.

During application the foil is brought into surface contact with the stationary phase, if necessary under application of pressure and heat. The reagent can migrate from the foil into the stationary phase by diffusion and effect the characteristic dyeing reaction there. The inverted procedure is possible, too, i.e., that the substances to be visualized reach the device via diffusion and the dyeing reaction takes place there. There will undoubtedly be cases where both reactions take place parallely.

According to a preferred embodiment of the present invention the device is built up in such a way that it can be fixed at the surface of the stationary phase of the chromatography plate.

For this purpose, at least that layer which is in contact with the stationary phase during application consists of a pressure-sensitive adhesive, a hotmelt adhesive, or is plastic or thermoplastic. In its simpliest embodiment the device may be single-layered.

However, according to a preferred embodiment of the invention the foil is multi-layered, and is a laminate from a carrier foil and at least one further foil layer. In this case, the carrier foil is free of reagent; the reagents are comprised in one or several further layers which are connected with the carrier foil.

The foil according to the present invention is flexible and preferably even stretchable, and, as a matter of fact, at least those parts of the device remaining on the chromatography plate after application have to be transparent.

Suitable materials for the reagent-containing foils or foil layers, respectively, are all foil-forming polymers compatible with the reagents, pressure-sensitive adhesive formulations, hotmelt sealings, thermoplastics, and elastomers. As examples are mentioned formulations on the basis of caoutchouc, polyisobutylene, polyethylene, polypropylene, polyacrylic acid derivatives, polyurethanes, polyvinyl acetates and their partially saponified derivatives, polyvinyl alcohols, polysiloxanes, polyamides, blockpolymers of styrene and another aliphatic olefin component, and copolymers of ethylene, vinylacetate, and acrylic acid derivatives.

In order to protect the reagent-containing layer, particulary for easy storage of the foil, it can be covered with a protective foil which naturally has to be removed prior to use. In case that the foil after its production is wound up as a roll and stored, the non-adhesive upper side of the carrier foil may have the function of a protective foil.

If the foil layer, which is in direct contact with the surface of the layer chromatogram when used, is self-adhesive, said protective foil, as a matter of fact, is to be rendered removable, e.g., by a silicone treatment. Other removable protective layers, e.g., consist of polytetrafluoroethylene, treated paper, cellophane, and the like.

Carrier foil and protective layer may consist of flexible or non-flexible material and may be built up single- or multi-layered. Suitable substances for their production, e.g., are polymeric substances, such as, e.g., polyethylene, polypropylene, polyvinyl chloride, polyester, polyacrylic acid derivatives, and polyamide. As further materials metal foils, e.g., an aluminium foil, alone or coated with a polymeric substrate, may be used, too.

The reagent or reagents may be contained in only one layer, it is also possible, however, that the reagent-containing part of the foil is built up multi-layered and that the individual layers comprise different reagents. This is suitable, if there are problems concerning the compatibility between the individual components, or if the reagents have to display their efficiency one after the other. If the latter is necessary, two foils according to the present invention may be employed one after the other. As a matter of fact, in this case, the carrier foil, if present at all, of the device applied firstly is to be removed, if it is not transparent and permeable to the reagents of the second device. Only in this case, it is suitable, as well, that the carrier foil of the device applied firstly is removed, if the then uncovered foil layer is self-adhesive.

The reagents themselves can be incorporated in the foils in different forms. For example, they can be present as molecularly disperse dissolved, crystalline, or microencapsulated. In case of several reagents lying side by side, these may also be incorporated in different forms. The device according to the present invention is used in the process for the visualization of substance stains on layer chromatograms in that the device is brought into contact with the stationary phase surface of the layer chromatogram, optionally under application of pressure and heat; said process also is a subject matter of the present invention.

Even if the device is rendered self-adhesive, pressure and heat favour the close contact to the stationary phase, and in most cases the heat leads to an enhanced dyeing reaction.

In the following, the present invention is illustrated but not limited by FIGS. 1 to 3 and the examples:

Figure 1:
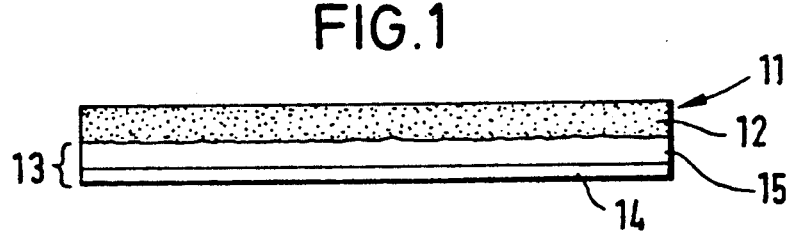
FIG. 1 represents the simplest embodiment of the invention, a single-layer, reagent-containing foil.

According to FIG. 1 the thermoplastic foil (11) comprises the reagents (12) in even distribution, which reagents are necessary to visualize the substance stains. When used, the foil is applied on the developed and dried chromatography plate, e.g., a thin-layer plate, and then the composite of thin-layer plate/foil is heated. The thin-layer plate itself consists of the carrier plate or carrier foil for the stationary phase (14) and of the stationary phase (15) itself. By melting or heating, respectively, the foil combines with the stationary phase (15), and the reagents of the foil reach the substance stains of stationary phase by diffusion. However, as mentioned above, the substances to be visualized can also diffuse into the foil, and thus the colour in the foil may be produced, too.

Figure 2:
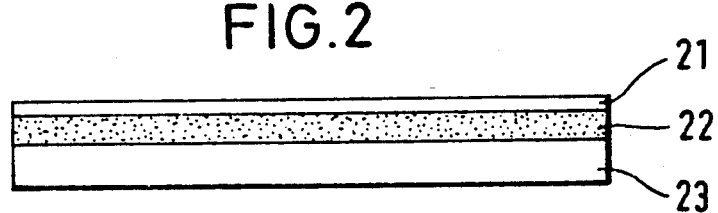
FIG. 2 represents a preferred, multi-layer foil

The preferred embodiment shown in FIG. 2 consists of a carrier foil (21), the actual reagent-foil (22) which preferably either is plastic, thermoplastic, or meltable, and of an additional protective foil (23) which is removed prior to use.

If a siliconized carrier foil is used, it is removed after use, and thus need not necessarily be transparent. According to a particularly preferred embodiment of the present invention the reagent-containing layer coming into contact with the stationary phase of the chromatography plate is a hotmelt coating, since in this case the contact to the stationary phase and to the substances to be visualized contained in the stationary phase is particularly intense. In this case, the stationary phase is penetrated by the reagent layer so to speak.

Figure 3:
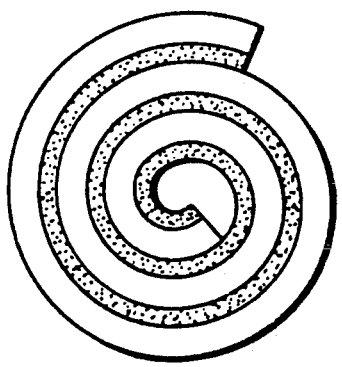
FIG. 3 shows a preferred, double-layer foil according to the present invention built up by a carrier and an adhesive reagent-containing layer.

According to FIG. 3 the upper side of the carrier foil has itself the function of the protective foil.

EXAMPLE 1

Non-self-adhesive device for the visualization of amino acids and amino sugars 107 g ethylene/vinyl acetate-copolymer (20% in methylene chloride) (Evatane 33.400, Messrs. ATOCHEM)

17.2 g paraffin (flash point 51°-53° C.) (25% in hexane)

1 g ninhydrin or isatin (dissolved in the lowest possible amount of methyl ethyl ketone)

are mixed, homogenized, and applied as a film of 100 μm thickness on a siliconized 100μ polyester foil, dried at 50° C. for 15 minutes. For storage purposes the reagent-layer is covered with another polyester foil serving as protective foil which, if possible, should be siliconized more strongly than the carrier foil.

The device is used as follows: For application, adequate pieces are placed on the thin-layer chromatography plate to be preserved and are pressed on at approximately 80° C. (on heating plate or drying oven). After melting (for approximately 30 seconds on a heating plate), it is cooled, and the siliconized polyester foil is removed. The colours of the substance stains are visible at approximately 80° C. after 10–20 seconds.

EXAMPLE 2

Self-adhesive device for the visualization of amino acids and amino sugars 33 g polyisobutylene (viscosity 10 9 Pa*s, 20° C.) (e.g., Oppanol B100, Messrs. BASF) 20% in benzine 66 g polyisobutylene (viscosity 25 Pa*s, 20° C.) (e.g., Oppanol B3, Messrs. BASF) 20% in benzine 0.25 g ninhydrin in 10 ml methylene chloride are mixed, homogenized, and applied on a siliconized polyester foil having a thickness of 100μ as film of 100μ thickness, dried at 50° C. for 15 minutes. Then, a polyester foil of 10μ thickness is laminated. For application, the siliconized polyester foil of 100μ thickness is removed from an adequate piece, and the reagent layer is glued on the developed and dried TLC-plate. After short heating, the substance stains become visible in their characteristic colours.

EXAMPLE 3

Device for visualization of basic substances 107 g ethylene/vinyl acetate-copolymer (Evatane 33.400, Messrs. ATOCHEM)

43 g paraffin (flame point: 51°-53° C.)

0.2 g methyl red are melted together, and a siliconized polyester foil of 100 μm thickness is coated with this mass in a thickness of 100μ. For application, adequate pieces are placed on the TLC-plate to be preserved, and are pressed on at approximately 100° C. (on heating plate or drying oven). After melting (approximately 1 minute on a heating plate) it is cooled, and the siliconized polyester foil is removed. The substance stains have a yellow colour on deep-red background.

EXAMPLE 4

Device for the visualization of heavy metal cations 100 g polyacrylate adhesive (40%) e.g., DUROTAK 280-2516, Messrs. National Starch
1.5 g nitrilotriethanol
1 g thioacetamide
are mixed, homogenized, applied as a film of 100μ thickness on a siliconized 100μ polyester foil, and dried at 50° C. for 15 minutes. Then the film is covered with a polyester foil having a thickness of 10μ and being unsiliconized and transparent. The further procedure corresponds to that described in example 3.

EXAMPLE 5

Device for the visualization of bivalent cations 100 g polyacrylate adhesive (40%) e.g. Durotak 280-2516, Messrs. National Starch
polyacrylate polymer with basic groups, e.g., 20 g Eudragit E 100 (Messrs. Röhm Pharma), 40% in acetic ester
0.1 g alizarin S
are mixed, homogenized, applied as film of 100μ on a siliconized 100μ polyester foil, and dried at 50° C. for 15 minutes. Then the film is covered with an unsiliconized, transparent polyester foil of 10μ thickness. The further procedure corresponds to that described in example 3.

I claim:

1. In the visualization of substance stains on a layer chromatogram wherein a reagent is applied to the chromatogram, the improvement wherein said reagent is carried on a foil, and said foil is applied to said chromatogram, whereby said chromatogram is dry and said reagent reacts with said dry chromatogram without further addition of a mobile phase.

2. The method according to claim 1, wherein the foil further carries an adhesive for adhesion to the chromatogram.

3. The method according to claim 1, wherein the foil comprises a polymeric material.

4. The method according to claim 3, wherein the polymeric material is selected from the group consisting of a polyamide, polyester, polyurethane or a homopolymer or copolymer of ethylene, propylene, vinyl chloride, vinyl acetate, vinyl alcohol, siloxane, an acrylate, isobutylene or styrene.

5. The method according to claim 3, wherein the polymeric material is coated onto aluminum foil.

6. The method according to claim 1, wherein the reagent is in the form of microcapsules.

7. The method according to claim 1, wherein the foil carries at least two different reagents in two different layers.

8. The method according to claim 1, wherein the foil initially carries a removable protective film on that face which will contact the layer chromatogram, the method including the step of removing said film prior to applying the foil to the chromatogram.

9. The method according to claim 1, including the further step of subjecting the foil, or chromatogram, or both to at least one of heat and pressure to effect visualization.

* * * * *